(12) United States Patent
Durbin et al.

(10) Patent No.: US 10,368,734 B2
(45) Date of Patent: Aug. 6, 2019

(54) METHODS AND SYSTEMS FOR COMBINED MORPHOLOGICAL AND ANGIOGRAPHIC ANALYSES OF RETINAL FEATURES

(71) Applicant: Carl Zeiss Meditec, Inc., Dublin, CA (US)

(72) Inventors: Mary K. Durbin, San Francisco, CA (US); Shamika Gune, Dublin, CA (US); Lin An, Walnut Creek, CA (US); Utkarsh Sharma, Dublin, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 407 days.

(21) Appl. No.: 15/046,878

(22) Filed: Feb. 18, 2016

(65) Prior Publication Data

US 2016/0242638 A1 Aug. 25, 2016

Related U.S. Application Data

(60) Provisional application No. 62/118,364, filed on Feb. 19, 2015.

(51) Int. Cl.
*A61B 3/14* (2006.01)
*A61B 3/00* (2006.01)
*A61B 3/10* (2006.01)
*A61B 3/02* (2006.01)
*A61B 3/113* (2006.01)

(52) U.S. Cl.
CPC ............ *A61B 3/0025* (2013.01); *A61B 3/102* (2013.01); *A61B 3/113* (2013.01)

(58) Field of Classification Search
CPC ........... A61B 3/113; A61B 3/103; A61B 3/14; A61B 3/152; A61B 3/1208; A61B 3/024; A61B 3/032; A61B 3/18; A61B 3/1015

USPC ....... 351/209, 200, 210, 205, 206, 208, 218, 351/221–223, 245–246
See application file for complete search history.

(56) References Cited

U.S. PATENT DOCUMENTS

| 5,640,220 A * | 6/1997 | Vo .............................. A61B 3/12 351/206 |
|---|---|---|
| 6,549,801 B1 | 4/2003 | Chen et al. |
| 7,301,644 B2 | 11/2007 | Knighton et al. |
| 8,433,393 B2 | 4/2013 | Sharma et al. |
| 8,857,988 B2 | 10/2014 | Sharma et al. |
| 2005/0171438 A1 | 8/2005 | Chen et al. |

(Continued)

OTHER PUBLICATIONS

Abramoff et al., "Retinal Imaging and Image Analysis", IEEE Reviews in Biomedical Engineering, vol. 3, 2010, pp. 169-208.

(Continued)

*Primary Examiner* — Dawayne Pinkney
(74) *Attorney, Agent, or Firm* — Morrison & Foerster LLP

(57) ABSTRACT

Methods and systems in ophthalmic imaging are presented that increase the sensitivity of automated diagnoses by the use of a combination of both functional and structural information derived from a variety of ophthalmic imaging modalities. An example method to analyze image data of an eye of a patient includes processing a first image dataset to obtain one or more functional metrics; processing a second image dataset to obtain one or more structural metrics; comparing the one or more structural metrics to the one or more functional metrics; and processing the results of said comparison to derive the probability of a disease or normality of the eye.

4 Claims, 11 Drawing Sheets

(56) References Cited

U.S. PATENT DOCUMENTS

| | | | |
|---|---|---|---|
| 2008/0025570 | A1 | 1/2008 | Fingler et al. |
| 2010/0027857 | A1 | 2/2010 | Wang |
| 2012/0274898 | A1 | 11/2012 | Sadda et al. |
| 2012/0277579 | A1 | 11/2012 | Sharma et al. |
| 2012/0307014 | A1 | 12/2012 | Wang |
| 2013/0176532 | A1 | 7/2013 | Sharma et al. |
| 2013/0301008 | A1 | 11/2013 | Srivastava et al. |
| 2014/0276025 | A1* | 9/2014 | Durbin .............. A61B 5/4842 600/427 |

OTHER PUBLICATIONS

An et al., "High-Resolution Wide-Field Imaging of Retinal and Choroidal Blood Perfusion with Optical Microangiography", Journal of Biomedical Optics, vol. 15, No. 2, Mar./Apr. 2010, pp. 026011-1-026011-9.

An et al., "In Vivo Vol.tric Imaging of Vascular Perfusion within Human Retina and Choroids with Optical Micro-Angiography", Optics Express, vol. 16, No. 15, Jul. 21, 2008, pp. 11438-11452.

An et al., "Optical Microangiography Provides Correlation between Microstructure and Microvasculature of Optic Nerve Head in Human Subjects", Journal of Biomedical Optics, vol. 17, No. 11, Nov. 2012, pp. 116018-1-116018-6.

Arend et al., "Contrast Sensitivity Loss is Coupled With Capillary Dropout in Patients with Diabetes", Investigative Ophthalmology & Visual Science, vol. 38, No. 9, Aug. 1997, pp. 1819-1824.

Arend et al., "The Relationship of Macular Microcirculation to Visual Acuity in Diabetic Patients", Archives of Ophthalmology, vol. 113, No. 5, May 1, 1995, pp. 610-614.

Bolz et al., "A Systematic Correlation of Angiography and High-Resolution Optical Coherence Tomography in Diabetic Macular Edema", Ophthalmology, vol. 116, No. 1, Jan. 2009, pp. 66-72.

Brar et al., "Correlation between Spectral-Domain Optical Coherence Tomography and Fundus Autofluorescence at the Margins of Geographic Atrophy", American Journal of Ophthalmology, vol. 148, No. 3, 2009, pp. 439-444.

Bresnick et al., "Abnormalities of the Foveal Avascular Zone in Diabetic Retinopathy", Archives of Ophthalmology, vol. 102, No. 9, Sep. 1984, pp. 1286-1293.

Choi et al., "Choriocapillaris and Choroidal Microvasculature Imaging with Ultrahigh Speed OCT Angiography", Plos One, vol. 8, Issue 12, Dec. 2013, pp. 1-8.

Chui et al., "Foveal Avascular Zone and its Relationship to Foveal Pit Shape", Optometry & Vision Science, vol. 89, No. 5, May 2012, pp. 602-610.

Chui et al., "Foveal Microvasculature and Its Relationship to Retinal Thickness", Investigative Ophthalmology & Visual Science, vol. 53, Mar. 2012, 3 pages.

Conrath et al., "Foveal Avascular Zone in Diabetic Retinopathy: Quantitative vs Qualitative Assessment", Eye, vol. 19, No. 3, Mar. 2005, pp. 322-326.

Dmuchowska et al., "Can Optical Coherence Tomography replace Fluorescein Angiography in Detection of Ischemic Diabetic Maculopathy?", Graefe's Archive for Clinical and Experimental Ophthalmology, vol. 252, No. 5, 2014, pp. 731-738.

Dubis et al., "Reconstructing Foveal Pit Morphology from Optical Coherence Tomography Imaging", British Journal of Ophthalmology, vol. 93, No. 9, Sep. 2009, pp. 1223-1227.

Enfield et al., "In Vivo Imaging of the Microcirculation of the Volar Forearm using Correlation Mapping Optical Coherence Tomography (CMOCT)", Biomedical Optics Express, vol. 2, 2011, pp. 1184-1193.

Ferguson et al., "Wide-Field Retinal Hemodynamic Imaging with the Tracking Scanning Laser Ophthalmoscope", Optics Express, vol. 12, No. 21, Oct. 18, 2004, pp. 5198-5208.

Fingler et al., "Mobility and Transverse Flow Visualization using Phase Variance Contrast with Spectral Domain Optical Coherence Tomography", Optics Express, vol. 15, No. 20, Sep. 18, 2007, pp. 12636-12653.

Fingler et al., "vol.tric Microvascular Imaging of Human Retina using Optical Coherence Tomography with a Novel Motion Contrast Technique", Optics Express, vol. 17, No. 24, Nov. 19, 2009, pp. 22190-22200.

Fischer et al., "Structural and Functional Changes of the Human Macula during Acute Exposure to High Altitude", PLoS One, vol. 7, Issue 4, Apr. 2012, pp. 1-8.

Gardiner et al., "Evaluation of the Structure-Function Relationship in Glaucoma", Investigative Ophthalmology & Visual Science, vol. 46, No. 10, Oct. 2005, pp. 3712-3717.

Gregori et al., "Spectral domain Optical Coherence Tomography imaging of Drusen in Nonexudative Age-Related Macular Degeneration", Ophthalmology, vol. 118, No. 7, Jul. 2011, pp. 1373-1379.

Grulkowski et al., "Scanning Protocols dedicated to Smart Velocity Ranging in Spectral OCT", Optics Express, vol. 17, Issue 26, Dec. 2009, pp. 23736-23754.

Hartnett et al., "Classification of Retinal Pigment Epithelial Detachments Associated with Drusen", Graefe's Archive for Clinical and Experimental Ophthalmology, vol. 230, No. 1, 1992, pp. 11-19.

Hong et al., "Three-Dimensional Visualization of Choroidal Vessels by using Standard and Ultra-High Resolution Scattering Optical Coherence Angiography", Optics Express, vol. 15, Issue 12, Jun. 2007, pp. 7538-7550.

Horii et al., "Relationship between Fluorescein Pooling and Optical Coherence Tomographic Reflectivity of Cystoid Spaces in Diabetic Macular Edema", Ophthalmology, vol. 119, Issue 5, May 2012, pp. 1047-1055.

Huang et al., "Optical Coherence Tomography", Science, vol. 254, Nov. 2, 1991, pp. 1178-1181.

Jia et al., "Split-Spectrum Amplitude-Decorrelation Angiography with Optical Coherence Tomography", Optics Express, vol. 20, No. 4, Feb. 13, 2012, pp. 4710-4725.

Kalloniatis et al., "Webvision: The Organization of the Retina and Visual System", Visual Acuity, May 1, 2005, 27 pages.

Kim et al., "In vivo Vol.tric Imaging of Human Retinal Circulation with Phase-Variance Optical Coherence Tomography", Biomedical Optics Express, vol. 2, No. 6, 2011, pp. 1504-1513.

Kim et al., "Noninvasive Imaging of the Foveal Avascular Zone with High-Speed, Phase-Variance Optical Coherence Tomography", Investigative Ophthalmology & Visual Science, vol. 53, No. 1, Jan. 2012, pp. 85-92.

Kita et al., "Relationship between Macular Ganglion Cell Complex Thickness and Macular Outer Retinal Thickness: a Spectral-Domain Optical Coherence Tomography Study", Clinical & Experimental Ophthalmology, vol. 41, Issue 7, Sep./Oct. 2013, pp. 674-682.

Klawitter "Speckle Variance Optical Coherence Tomography for Imaging Microcirculation", Student Conference Medical Engineering Science 2013: Proceedings, vol. 2, 2013, 4 pages.

Lee et al., "Automated Characterization of Pigment Epithelial Detachment by Optical Coherence Tomography", Investigative Ophthalmology & Visual Science, vol. 53, No. 1, Jan. 2012, pp. 164-170.

Liu et al., "Automatic Retinal Vessel Segmentation based on Active Contours Method in Doppler Spectral-domain Optical Coherence Tomography", Journal of Biomedical Optics, vol. 18, Issue 1, Jan. 2013, pp. 016002-1-016002-4.

Liu et al., "Real-Time Bulk-Motion-Correction free Doppler Variance Optical Coherence Tomography for Choroidal Capillary Vasculature Imaging", Optics Express, vol. 19, Issue 4, 2011, pp. 3657-3666.

Mahmud et al., "Review of Speckle and Phase Variance Optical Coherence Tomography to Visualize Microvascular Networks", Journal of Biomedical Optics, vol. 18, Issue 5, Apr. 24, 2013, pp. 050901-1-050901-13.

Makita et al., "Optical Coherence Angiography", Optics Express, vol. 14, No. 17, 2006, pp. 7821-7840.

Mariampillai et al., "Optimized Speckle Variance OCT Imaging of Microvasculature", Optics Express, vol. 35, No. 8, Apr. 15, 2010, pp. 1257-1259.

Mariampillai et al., "Speckle Variance Detection of Microvasculature using Swept-Source Optical Coherence Tomography", Optics Letters, vol. 33, No. 13, Jul. 1, 2008, pp. 1530-1532.

(56) References Cited

OTHER PUBLICATIONS

Nam et al., "Complex Differential Variance Algorithm for Optical Coherence Tomography Angiography", Biomedical Optics Express, vol. 5, 2014, pp. 3822-3832.
Otani et al., "Correlation between Optical Coherence Tomography and Fluorescein Angiography Findings in Diabetic Macular Edema", Ophthalmology, vol. 114, Issue 1, Jan. 2007, pp. 104-107.
Sakata et al., "Relationship between Macular Microcirculation and Progression of Diabetic Macular Edema", Ophthalmology, vol. 113, No. 8, Aug. 2006, pp. 1385-1391.
Sakata et al., "Relationship of Macular Microcirculation and Retinal Thickness with Visual Acuity in Diabetic Macular Edema", Ophthalmology, vol. 114, No. 11, Nov. 2007, pp. 2061-2069.
Sayegh et al., "A Systematic Comparison of Spectral-Domain Optical Coherence Tomography and Fundus Autofluorescence in Patients with Geographic Atrophy", American Academy of Ophthalmology, vol. 118, No. 9, 2011, pp. 1844-1851.
Springer et al., "Development of the Primate Area of high Acuity, 3: Temporal Relationships between Pit Formation, Retinal Elongation and Cone Packing", Visual Neuroscience, vol. 22, Issue 2, Mar. 2005, pp. 171-185.
Springer et al., "Development of the Primate Area of High Acuity. 1. Use of Finite Element Analysis Models to identify Mechanical Variables affecting Pit Formation", Visual Neuroscience, vol. 21, Issue 01, Jan. 2004, pp. 53-62.
Springer et al., "Development of the Primate Area of high Acuity. 2. Quantitative Morphological Changes Associated with Retinal and Pars Plana Growth", Visual Neuroscience, vol. 21, Issue 5, Sep. 2004, pp. 775-790.
Stetson et al., "OCT Minimum Intensity as a Predictor of Geographic Atrophy Enlargement", Investigative Ophthalmology & Visual Science, vol. 55, No. 2, Feb. 10, 2014, 1 page.
Stewart et al., "The Dual-Bootstrap Iterative Closest Point Algorithm with Application to Retinal Image Registration", IEEE Transactions on Medical Imaging, vol. 22, No. 11, Nov. 2003, pp. 1379-1394.
Tao et al., "Velocity-resolved 3D Retinal Microvessel Imaging using Single-Pass Flow Imaging Spectral domain Optical Coherence Tomography", Optics Express, vol. 17, Issue 5, Mar. 2009, pp. 4177-4188.
Tick et al., "Foveal Shape and Structure in a Normal Population", Investigative Ophthalmology & Visual Science, vol. 52, Jul. 2011, pp. 5105-5110.
Tyrberg et al., "Multifocal Electroretinogram (mfERG) in Patients with Diabetes Mellitus and an Enlarged Foveal Avascular Zone (FAZ)", Documenta Ophthalmologica, vol. 117, Issue 3, Nov. 2008, pp. 185-189.
Vakoc et al., "Three-Dimensional Microscopy of the Tumor Microenvironment in Vivo using Optical Frequency Domain Imaging", Nature Medicine, vol. 15, No. 10, Oct. 2009, pp. 1219-1223.
Wang et al., "Depth-Resolved Imaging of capillary Networks in Retina and Choroid using Ultrahigh Sensitive Optical Microangiography", Optics Express, vol. 35, No. 9, May 1, 2010, pp. 1467-1469.
Wang et al., "Frequency Domain Phase-Resolved Optical Doppler and Doppler Variance Tomography", Optics Communications, vol. 242, 2004, pp. 345-350.
Wang et al., "Optical Microangiography provides Depth-Resolved Images of Directional Ocular Blood Perfusion in Posterior Eye Segment", Journal of Biomedical Optics, vol. 15, Issue 2, Mar./Apr. 2010, pp. 020502-1-020502-3.
Wang et al., "Three Dimensional Optical Angiography", Optics Express, vol. 15, No. 7, Apr. 2, 2007, pp. 4083-4097.
Yehoshua et al., "Comparison of Geographic Atrophy Measurements from the OCT Fundus Image and the Sub-RPE Slab Image", Ophthalmic Surgery, Lasers & Imaging Retina, vol. 44, No. 2, Mar./Apr. 2013, pp. 127-132.
Yu et al., "Doppler Variance Imaging for Three-Dimensional Retina and Choroid Angiography", Journal of Biomedical Optics, vol. 15, No. 1, Jan./Feb. 2010, pp. 016029-1-016029-4.
Zayit-Soudry et al., "Retinal Pigment Epithelial Detachment", Survey of Ophthalmology, vol. 52, No. 3, May-Jun. 2007, pp. 227-243.
Zhao et al., "Doppler Standard Deviation Imaging for Clinical Monitoring of in vivo Human Skin Blood Flow", Optics Express, vol. 25, No. 18, Sep. 15, 2000, pp. 1358-1360.
Zhu et al., "Predicting Visual Function from the Measurements of retinal Nerve Fiber Layer Structure", Investigative Ophthalmology & Visual Science, vol. 51, No. 11, Nov. 2010, pp. 5657-5666.

\* cited by examiner

901

1001

1101  1102

1301

METHODS AND SYSTEMS FOR COMBINED MORPHOLOGICAL AND ANGIOGRAPHIC ANALYSES OF RETINAL FEATURES

PRIORITY

This application claims priority to U.S. Provisional Application Ser. No. 62/118,364, filed Feb. 19, 2015, the entire disclosure of which is incorporated herein by reference.

TECHNOLOGICAL FIELD

The present application concerns improved and automated diagnoses of ocular pathologies using the combined information derived from structural and functional imaging modalities.

BACKGROUND

Structural imaging of morphological or anatomical features of the retina of an eye of a patient can reveal information regarding the state of the eye and even a prognosis for disease. Some of the features can be due to pathologies such as diabetic retinopathy (DR), aged-related macular degeneration (AMD), a detachment of the retinal pigment epithelium from its basement membrane (PED), accumulations of lipids (exudates; drusen), and poorly phagocytized photoreceptor outer segments. Alternative imaging methods, deriving more dynamic or functional information can also be used to identify problem areas. The information obtained from functional imaging can augment and/or supplement that of structural imaging information.

Diabetic retinopathy is one of the major causes of legal blindness in the industrially developed world. The most common vision threatening complication of diabetic retinopathy is diabetic maculopathy incorporating diabetic macular edema and macular ischemia (microangiopathy), caused by hyperglycemic-initiated cellular changes. A structural hallmark of diabetic retinopathy or of diabetic maculopathy is in the appearance of vascular changes such as microaneurysms and capillary occlusions. Commonplace responses to DR such as laser surgery usually only begin when severe damage has occurred to the retinal structure detected by an optical imaging system, or when the patient is experiencing a functional vision deficit.

Often structural information of the retina is obtained using a variety of optical techniques to aid in diagnosing the existence and progression of the disease. Structural information or metrics can be the thicknesses of various retinal layers; or can be morphological in nature, with identifiable alterations in the appearance of the vasculature or of the retina.

The identification of a limited set of retinal problems is made possible by analyses of images of the fundus, using one or more of the many fundus imaging modalities such as scanning laser ophthalmoscopy (or a confocal version thereof), or by optical coherence tomography (OCT; see for example, Huang et al. 1991), which can provide three-dimensional structural information, especially that of the retina.

An important anatomical region of the eye is that of the macula, depicted in the 2D image of FIG. 1a. Macular subregions have their own identifications, such as the fovea, foveal avascular zone (FAZ), the foveal pit, and the foveola. Many pathologies of the eye are identified by analysis of optical images of this region.

Retinal layers, depicted in the OCT image of FIG. 1b, normally consist of the retinal nerve fiber layer (RNFL or NFL), the ganglion cell layer (GCL), the inner plexiform layer (IPL), the inner nuclear layer (INL) containing the somae (cell bodies) of the bipolar, amacrine, horizontal, and Mueller cells, the outer plexiform layer (OPL), the outer nuclear layer (ONL) containing the somae of the photoreceptors, and the outer segments (OS) and inner segments (IS) of the photoreceptors. The external or outer limiting membrane (ELM or OLM) is the layer between the nuclei of the photoreceptors and their inner segments. The outer segments are embedded into the villi of the cells forming the retinal pigment epithelium (RPE) which itself is attached to the basement membrane.

Alternatively, functional imaging can reveal different aspects of retinal diseases, especially in the case of DR. Functional information, traditionally blood flow, may be derived using a variety of techniques such as the invasive fluorescein angiography (using injectable toxic dyes) and Doppler optical coherence tomography (D-OCT), which is limited in its applicability for functional imaging of the capillary network due to a near orthogonal Doppler angle.

A relatively new technique, using optical coherence tomography (OCT), is able to provide functional information by processing multiple images taken over time using intensity and/or phase fluctuations to highlight motion, such as blood flow within vessels. Thus functional information can be derived for flow in the retinal vasculature, as well as flow within the choroidal vasculature. And, OCT provides depth information, unlike the traditional angiography associated with a fundus imaging modality. These uses of OCT are collectively labelled as OCT Angiography (OCT-A) or functional OCT.

Foveal Avascular Zone (FAZ)

The anatomic macula is defined as that area of the posterior retina having at least two layers of nuclei in the ganglion cell layer. Clinically, this area extends 6 to 7 mm from the temporal edge of the optic nerve. FIG. 1b depicts an OCT scan of retina including the fovea (indicated by 101 in FIG. 1b) obtained with an optical coherence tomographic system (OCT).

A typical anatomic fovea is 1.5 mm in diameter and centered 4 mm temporal and 0.5 mm inferior to the center of the optic nerve head. The inner retinal surface of the fovea is typically concave in a healthy eye. There are typically no blood vessels in the central fovea in a healthy eye. This capillary-free zone in the fovea is 400 to 500 µm in diameter, and is called the foveal avascular zone (FAZ).

The center of the fovea is the foveola or foveal pit. It is roughly 350 µm in diameter and is contained within the foveal avascular zone. At this center, it is free of cells except for red and green cone photoreceptors. In the portion of the fovea surrounding the foveola, these layers: RNFL, GCL+ IPL, and INL, are not present (although in shallow foveal pits, the INL may be continuous underneath the foveola). The disappearance of these layers at the foveal boundary can be seen in FIG. 1b. The layers of the ONL and below are the only ones present in this particular fovea.

The FAZ has been extensively studied in the past (see for example, Bresnick et al. 1984; Arend et al. 1995/1997; Sakata et al. 2006/2007; Chui et al. 2014; Tyrberg et al. 2008; Otani et al. 2007; Kim et al. 2012; Bolz et al. 2009; Springer & Hendrickson 2004a/2004b/2005; Tick et al. 2011; Dubis et al. 2009; Dmuchowska et al. 2012; and references cited within all of these citations). When DR is present, the FAZ area may be enlarged due to a disturbed macular circulation (i.e., a functional characteristic). These changes have been shown to be clinically significant in association with the progression of the disease and to result in macular ischemia (with the concomitant loss of visual function and acuity), disturbed electroretinograms, decreased contrast sensitivity, and visual field defects. There have been reports demonstrating an altered vascular function shown by a fluorescein angiographic image and neuroglial pathomorphology as depicted by OCT. Previous studies have shown reduced capillary blood flow, decreased capillary density in diabetic patients and also have demonstrated that progressive capillary loss in the FAZ was related to decreased visual acuity in these patients.

PED: Retinal Pigment Epithelium Detachment

Detachment of the retinal pigment epithelium is characteristic of a variety of chorio-retinal diseases including age-related macular degeneration (see for example Zayit-Soudry et al. 2007). Various types of pigment epithelial detachments (PEDs) have been identified including serous, fibrovascular, and drusenoid among others (see, e.g., Hartnett et al. 1992). Optical coherence tomography (OCT) has provided a way to visualize, segment, and classify PEDs (see for example, Stetson et al. 2013).

AMD: Age-related Macular Degeneration

Age related macular degeneration (AMD) results in the loss of visual acuity typically resulting from progressive degeneration of the choriocapillaris, the RPE, and photoreceptors. However, the earliest manifestation of the disease is likely to be a disruption of the basement membrane (see for example, Hageman 2015). Progressed levels of the disease are identifiable by the submacular neovascularization, geographic atrophy (normally related to a complete loss of the RPE, potentially together with loss of the chorio-capillaris, and photoreceptors). The disease normally begins in the dry form and may progress to geographic atrophy or a 'wet' or neovascularized version. In the presence of neovascularization, there is an accumulation of fluid, hemorrhage, and lipid exudation within the macula that can result in fibrosis, which is referred to as a disciform scar.

Exudates

Exudates are accumulations of lipids or lipid residues that have leaked from damaged capillaries. The most prevalent cause is from diabetes. Other causes can be retinal vein occlusion, hypertensive retinopathy, angiomas (von Hippel-Lindau disease), other vascular dysplasias, and radiation-induced vasculopathy.

SUMMARY

Embodiments of the present application combine structural and functional imaging information into metrics that are more sensitive to the existence and progression of disease than either structural or functional information alone would reveal. For example, while thickness measurements of the various retinal layers can provide useful information, these are limited in scope and are not optimal for early detection and for measuring disease progression.

An exemplary use of these embodiments is in the ability to identify eyes that are diseased due to diabetic retinopathy, by the comparison of diameters of the foveal avascular zone derived from functional analysis of imaging data of the retina with that derived from a structural analysis. It is well known that, in this particular case, FAZ diameters either structurally or functionally derived, when taken separately have a large variance in normal eyes, which would make differentiating normal from diseased eyes less sensitive. However, these two diameters (functional and structural) are very likely to be closely linked in normal eyes because the vasculature supplies the metabolic needs of the tissue that is present. By comparing the two metrics (areas or diameters of FAZ) obtained from functional and from structural imaging modalities, the ability to discriminate between normal and diseased eyes will improve, since the comparison is expected to have a smaller variance in normals. That is, by comparing the two metrics (areas or diameters of FAZ) obtained from functional and from structural imaging modalities, the ability to discriminate between normal and diseased eyes obviates lack of sensitivity caused by the large variance present in either of the structural and functional determinations. It is often found that a metric that combines two inputs has variability at least as large as the largest variability of the two inputs, but the FAZ size is expected to differ from this usual rule. The variance in FAZ size in normal eyes is due to the fact that good vision is achievable with a wide array of FAZ sizes, but the relationship of the microcirculation around the fovea to the tissue in the fovea is driven by metabolic requirements, and therefore may have substantially less variability in the population than the variability of one of the inputs.

The basic embodiment of the present application can be extended to other pathologies, such as PED, exudates, and AMD. Thus combined analyses from both imaging classes (structural and functional) can yield new and valuable insights into retinal disease existence and progression. The metrics defined can be optimally correlated with the prevalence, extent, severity of disease, or alternatively, just a metric which correlates with normalcy.

A variety of imaging modalities can be used to obtain data in order to identify and measure features or pathologies found. A preferred embodiment uses both structural and functional OCT datasets from which structural and functional metrics can be obtained (via automatic or manual methods), combined and analyzed, or input into an expert system in order to obtain a reliable indication of the presence of disease or the likelihood of its progression. An exemplary expert system could be based on a support vector machine (SVM). Other applicable classifiers would be k-nearest neighbor, naïve Bayesian, neural networks, and decision trees.

A more preferred embodiment is obtaining a single OCT dataset, containing scans or data taken at approximately the same location over times, that can be processed in two different ways: one for structural information and one for functional information: each of which can be analyzed for respective metrics. Such an approach will naturally improve clinical efficiency.

DETAILED DESCRIPTION

All patent and non-patent references cited within this specification are herein incorporated by reference in their entirety to the same extent as if the disclosure of each individual patent and non-patent reference was specifically and individually indicated to be incorporated by reference in its entirely.

Figure 1A:
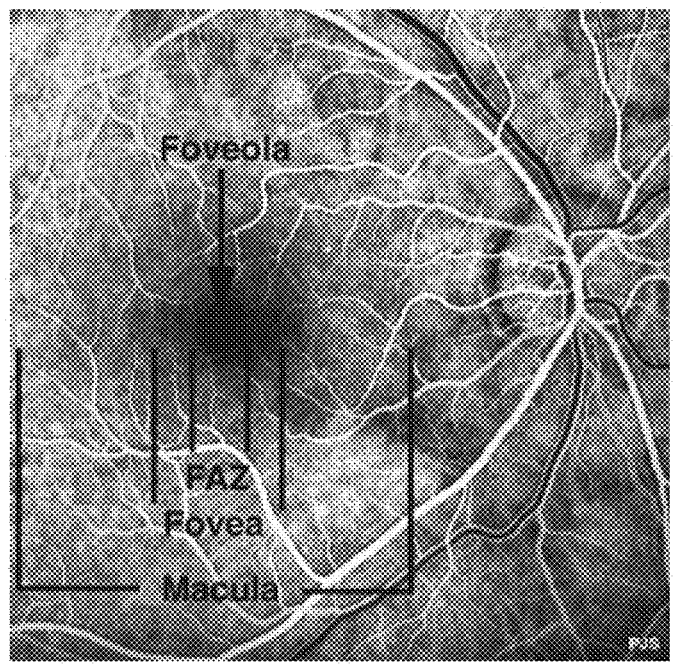
FIG. 1a is an image of the macula showing the large-scale anatomical regions.
Figure 1B:
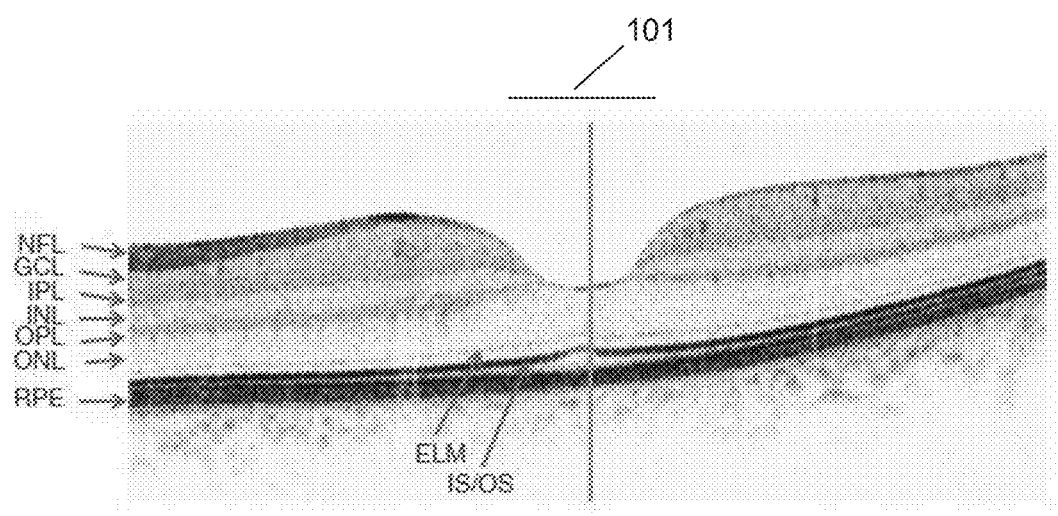
FIG. 1b is an OCT B-scan through the fovea (101) of an eye of a patient. The various retinal layers have been marked for identification.
Figure 2:
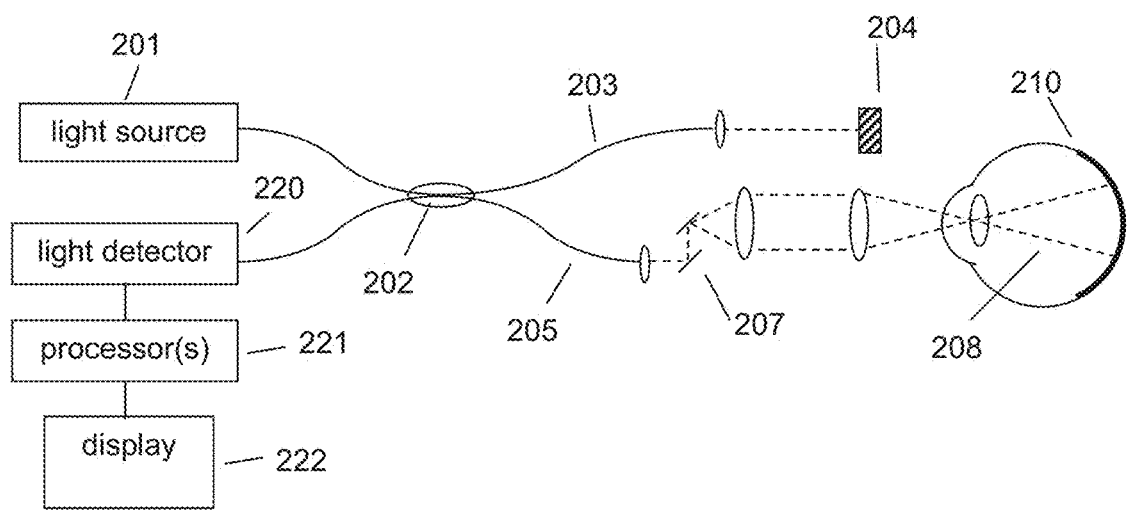
FIG. 2 is a schematic of a basic OCT imaging system.

A diagram of a generalized OCT system is shown in FIG. 2. Light from source 201 is routed, typically by optical fiber 205, to illuminate the sample 210, a typical sample being tissues in the human eye. The source 201 can be either a broadband light source with short temporal coherence length in the case of SD-OCT or a wavelength tunable laser source in the case of SS-OCT. The light is scanned, typically with a scanner 207 between the output of the fiber and the sample, so that the beam of light (indicated by dashed line 208) is scanned laterally (in x and y) over the area or volume to be imaged. Light scattered from the sample 210 is collected, typically into the same fiber 205 used to route the light for sample illumination. Reference light derived from the same source 201 travels a separate path, in this case involving fiber 203 and retro-reflector 204 with an adjustable optical delay. Those skilled in the art recognize that a transmissive reference path can also be used and that the adjustable delay could be placed in the sample or reference arm of the interferometer. Collected sample light is combined with reference light, typically in a fiber coupler 202, to form light interference in a detector 220. Although a single fiber port is shown going to the detector 220, those skilled in the art recognize that various designs of interferometers can be used for balanced or unbalanced detection of the interference signal. The output from the detector is supplied to a processor 221. The results can be stored in one or more processors 221 (which can include parallel processors such as GPUs or FPGAs) or displayed on display 222. The processing and storing functions may be localized within the OCT instrument or functions may be performed on an external processing unit to which the collected data is transferred. This unit could be dedicated to data processing or perform other tasks which are quite general and not dedicated to the OCT device. The processor may contain for example a field-programmable gate array (FPGA), a digital signal processor (DSP), an application specific integrated circuit (ASIC), a graphics processing unit (GPU), a system on chip (SoC) or a combination thereof, that performs some, or the entire angiography data processing steps, prior to passing on to the host processor or in a parallelized fashion. Using multiple processors allows the processing to attain structural metrics and the processing to attain functional metrics to be separate and possibly to operate in parallel.

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to any type of OCT system capable of generating data for OCT angiography analysis including parallel OCT techniques such as multi-spot, line-field, partial-field, and full-field.

In Fourier Domain optical coherence tomography (FD-OCT), each measurement is the real-valued spectral interferogram ($S_j(k)$). The real-valued spectral data typically goes through several postprocessing steps including background subtraction, dispersion correction, etc. The Fourier transform of the processed interferogram, results in a complex valued OCT signal output $A_j(z)=|A_j|e^{i\varphi}$. The absolute value of this complex OCT signal, $|A_j|$, reveals the profile of scattering intensities at different path lengths, and therefore scattering as a function of depth (z-direction) in the sample. Similarly, the phase, $\varphi_j$ can also be extracted from the complex valued OCT signal. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. We use the term "cluster scan" herein to refer to a single unit or block of data generated by repeated acquisitions at the same location for the purposes of analyzing functional information from the image data. A cluster scan can consist of multiple A-scans or B-scans collected over time at approximately the same location on the sample. A variety of ways to create B-scans are known to those skilled in the art including but not limited to along the horizontal or x-direction, along the vertical or y-direction, along the diagonal of x and y, or in a circular or spiral pattern. The majority of the examples discussed herein refer to B-scans in the x-z dimensions but the invention would apply equally to any cross sectional image.

Equivalent terminology is sometimes used in the literature. An M-scan consists of multiple A-scans taken over time at the same transverse location. A MB-scan is used to describe multiple M-scans taken over different transverse positions to create a 2D OCT image of M-Scans. A BM-scan is multiple B-scans taken over time for the same transverse scan region (see for example, Makita et al. 2006; Fingler et al. 2007).

Structural OCT

OCT has the ability to image the different retinal tissues such as the internal limiting membrane (ILM), RNFL, GCL, IPL, INL, OPL, ONL, ELM, junction between the IS and OS, RPE, Bruch's membrane, and the choroid. Moreover with OCT data, the segmentation and further analyses of morphological pathologies such as, e.g., drusen and geographic atrophy etc., also augment the usefulness of this modality (See, e.g., Gregori et al. 2011; Yehoshua et al. 2013).

In addition, OCT images permit the ability to identify many retinal pathological areas such as macular edema, macular detachment, macular hole, central serous retinopathy, and elevated RPE. In the last case, often referred to as pigment epithelial detachment (PED), the cause may be serous fluid, fibrovascular tissue, hemorrhage, or the coalescence of drusen beneath the RPE. Although PEDs can occur in the context of non-neovascular age-related macular degeneration, most, however, are related to choroidal neovascularization (CNV). This neovascularization can spread and cause fluid accumulation away from the CNV to create a serous PED. Thus, it is considered that PED's are at least a subset of problems associated with RPE elevation.

OCT characteristic information derivable from the aforementioned OCT imaging modalities (or optical coherence imaging modalities) include, but are not limited to: thicknesses of the various retinal layers; volumetric information regarding drusen (3D size)—an early indicator of age-related macular degeneration; extent of retinal thickening or the hard exudates associated therewith; the extent of diabetic macular edema; extent of macular edema due to retinal vein occlusion; extent of diseases of the vitreomacular interface such as epiretinal membranes; the extent of macular holes, pseudoholes, schisis from myopia or optic pits; the extent of serous chorioretinopathy; the extent of retinal detachment; characteristics of the optic nerve head including disc size, neuro-retinal rim area, and cup-to-disc ratio; extent or area of peripapillary atrophy; extent or area of geographic atrophy; extent of blood flow in the retina; the extent of vascular perfusion or lack thereof; and with repeated measurements of a similar kind, chronological changes that can help suggest prognosis or progression.

Functional OCT

Functional OCT can provide important clinical information that is not available in the typical intensity-based structural OCT images. OCT Angiographic (OCT-A) imaging modalities have been recently developed which not only provide high spatial and temporal resolution, but depth information as well, thus enabling the mapping of the retinal vasculature or regions of flow within tissue. OCT-A provides a non-invasive technique to visualize and indirectly quantify the integrity of retinal circulation pathways.

There have been several functional or contrast enhanced methods including Doppler OCT, Phase-sensitive OCT measurements, Polarization Sensitive OCT, Spectroscopic OCT, complex, intensity, and speckle-based OCT measurements, nanoparticle contrast-enhanced OCT, second harmonic generation OCT, etc. Integration of functional extensions can greatly enhance the capabilities of OCT for a range of applications in medicine. This class involves the ability to study motion and flow including but not limited to blood flow and perfusion, oxygen perfusion, metabolic processes such as consumption of energy, conversion of glucose into ATP, utilization of ATP especially by the mitochondria, and the like.

In OCT Angiography (a.k.a. Functional OCT, optical microangiography, motion contrast OCT), changes between the OCT data collected at the same location at different times (cluster scans) are used to analyze motion or flow in the sample using any one of a multitude of motion contrast algorithms (see for example US Patent Publication Nos. 2005/0171438, 2012/0307014, 2010/0027857, 2012/0277579, U.S. Pat. No. 6,549,801, Mariampillai et al., "Speckle variance detection of microvasculature using swept-source optical coherence tomography", Optics Letters 33(13), 1530-1533, 2008, Enfield et al., "In vivo imaging of the microcirculation of the volar forearm using correlation mapping optical coherence tomography" (cmOCT), Biomed. Opt. Express 2(5), 1184-1193, 2011, Nam et al. "Complex differential variance algorithm for optical coherence tomography angiography" Biomedical Optics Express 5(11) 3822-3832 2014, and Jia et al. "Split-spectrum amplitude decorrelation angiography with optical coherence tomography" Optics Express 20(4) 4710-4725 (2012), the contents of which are hereby incorporated by reference). Motion contrast algorithms can be applied to the intensity information derived from the OCT image data (intensity-based algorithm), the phase information from the OCT image data (phase-based algorithm), or the complex OCT image data (complex-based algorithm).

One of the major applications of such techniques has been to generate enface vasculature images of the retina. Enface images are typically generated from three dimensional data cubes by summing pixels along a given direction in the cube, either in their entirety or from sub-portions of the data volume (see for example U.S. Pat. No. 7,301,644). Visualization of the detailed vasculature using functional OCT enables clinicians to obtain new and useful clinical information for diagnosis and management of eye diseases in a non-invasive manner.

Fundus Imaging

Fundus imaging of the eye is basically a 2D projection of the 3D retina using light reflected off the retina. The light can be monochromatic or polychromatic, depending upon the desire to enhance certain features or depths. There are various instrumental approaches to fundus imaging. These include, but are not limited to, fundus cameras, scanning laser ophthalmoscopes (SLO), line scanning ophthalmoscopes (LSO), biomicroscopy, fluorescein (FA) or indocyanine green (ICG) angiography, scanning laser polarimetry (SLP), fundus auto-fluorescence (FAF), confocal scanning laser ophthalmoscopes (cSLO), and broad line fundus imaging (BLFI). Variety of wavelengths can be used in the scanning beam (NIR, color, RGB, RGB-splits). Stereo fundus imaging is obtainable via combining separate images taken at different angles. FA could also be achieved by taking sequential images (i.e., FA movie or movies). A live FA image is also possible (OPMI-display).

Several of the aforementioned fundus imaging modalities are of a functional nature (see, e.g., Ferguson et al. 2004), which permit understandings or insight into neuroanatomical basis of psychophysical and pathophysiological phenomena. Functional observations can include detection of ischemic regions, evaluation of biochemical changes associated with various pathological conditions, localization of drugs and efficacy thereof, blood flow, glucose utilization, oxygen utilization, and other metabolic processes and molecules.

It should be noted that the term 'fundus imaging' (or fundus imaging modality) will be referred to hereinafter as any aforementioned system to image the fundus of an eye (see, e.g., Abramoff et al. 2010). The class of functional fundus imaging modalities refers to FA, ICG, Doppler, oximetry, FAF, and any other mode which measures blood flow or perfusion, oxygen flow or perfusion, metabolic processes, consumption of energy, conversion of glucose into adenosine triphosphate (ATP), utilization of ATP especially by mitochondria, activity of lysosomes, oxidation of fatty acids, and the like. Fluorescein or indocyanine green angiography are modes of functional fundus imaging which use fluorophores that are injected into the blood stream of a patient (or ingested orally). As time progresses, these fluorophores reach the blood vessels of the eye. Subsequently, upon examination of the retina of an eye within a certain wavelength band, the circulation pattern can be observed due to the emission from the photon-stimulated fluorophores.

Another functional mode is that of fundus autofluorescence and is based on the fluorescence of lipofuscin in the retinal pigment epithelium (hereinafter, RPE). Lipofuscin is a residue of suboptimally phagocytosed photoreceptor outer segments (non-degradable intralysosomal substances). FAF's principal use is in detecting pathological changes in the RPE, which include, but are not limited to, macular pigments, photopigments, and macrophages in the subretinal space.

FAF is also a popular method for imaging of geographic atrophy (GA), which is characterized by the loss of various retinal layers, including outer nuclear layer, external limiting membrane, inner and even outer segments of photoreceptors, down to the RPE. This pathological disturbance can manifest itself as a morphological feature identified via hypopigmentation/-depigmentation due to the absence of the retinal pigment epithelium. Depending on the wavelength of light used for stimulation, autofluorescence images may suffer from loss of signal near the fovea, a problem that does not occur in OCT visualization of GA. Certain patterns of autofluorescence at the margin of GA have been shown to correlate with faster progression of the pathologies associated with GA.

OCT can detect retinal layer disruption at the borders of geographic atrophy (see for example, Brar et al. 2009), and those patterns of disruption have been shown to be related to patterns of hyperautofluorescence (see for example, Sayegh et al. 2011).

For the purposes of the present application, the term functional imaging or functional imaging modality shall refer to any of the aforementioned functional imaging modalities, whether it be under the rubric of optical coherence tomography imaging or within the rubric of fundus imaging.

Diagnostic Information from Fundus Imaging

Fundus characteristic information derivable from fundus imaging modalities include, but are not limited to: extent of drusen, geographic atrophy, hard and soft exudates, cotton-wool spots, blood flow, ischemia, vascular leakage, reflectivities as a function of depth and wavelength; hyper- or hypo-pigmentation abnormalities (often due to the absence of melanin or the presence of lipofuscin); colors based on relative intensities at different wavelengths; and chronological changes in any of these. The extent of many of these observables is directly correlated with the likelihood of the presence of disease, as is well known in the art.

OCT and Fundus Structural and Functional Metrics

Figure 3A:
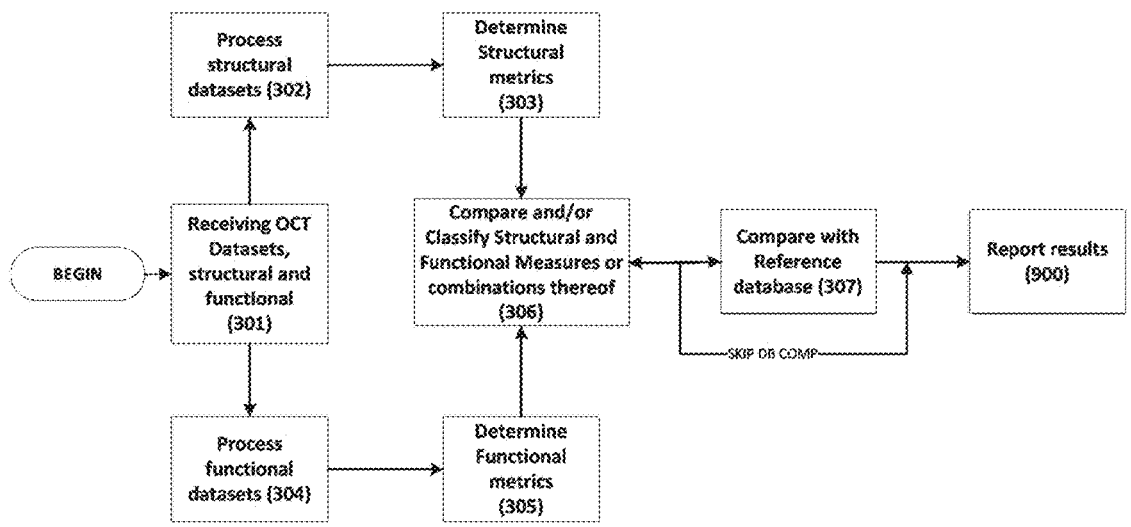
FIG. 3a is a flow chart of one embodiment of the present application, in which one or more datasets from a variety of OCT imaging modalities are input to the method, and structural and functional measurements are derived therefrom.

FIG. 3a presents a basic embodiment in which two or more OCT datasets are obtained (301) by different OCT imaging modalities, and results derived therefrom. In this case, each dataset taken with a certain OCT modality is processed in a certain manner, based upon well-known techniques for that particular modality. The data for the two modalities (i.e., structural and functional modalities) can be collected with the same OCT system or with different systems dedicated to each modality.

In the method of FIG. 3a, the OCT dataset taken for structural measurements is processed (302) into a resultant image or images and then structural metrics (303) are measured or derived therefrom. Structural observables or metrics can be measured, either automatically, or measured manually.

The OCT functional dataset is processed (304) in one of the several ways appropriate for functional OCT data as described above. After processing of the appropriate dataset for functional observations, functional metrics (305) can be obtained, either automatically or manually.

Figure 3B:
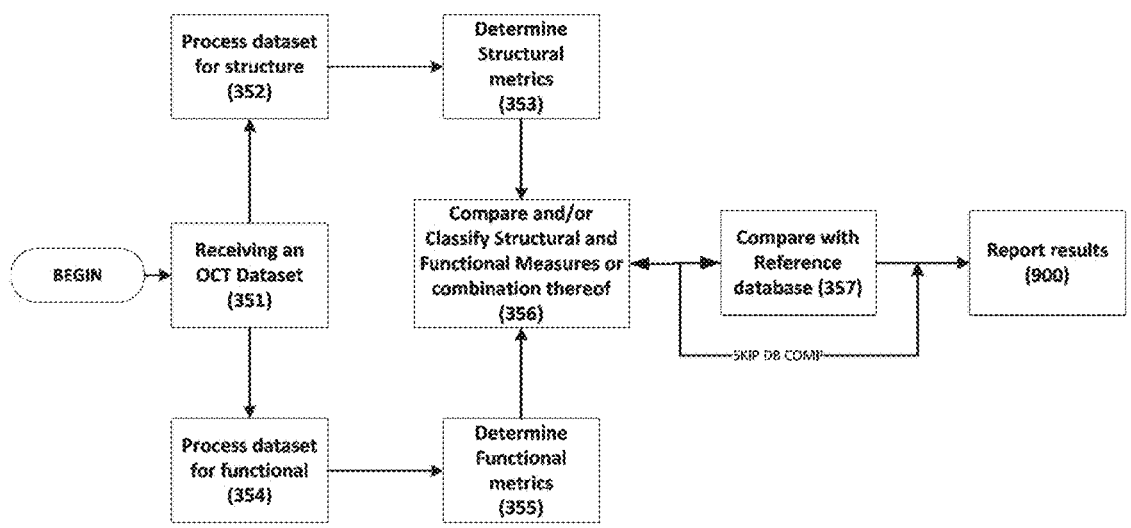
FIG. 3b is a flow chart of another embodiment of the present application, in which a single OCT dataset is processed two different ways to be able to make structural and functional measurements.

FIG. 3b presents a basic embodiment using a single OCT image dataset (351), and this dataset is processed in two different ways: one so that structural information (352) can be derived, and the other so that functional data (354) can be derived. From the structural processing of the dataset, structural metrics (353) can be obtained, such as, e.g., thicknesses of the various retinal layers. From the functional processing of the dataset, functional metrics (355) can be determined, such as blood flow or flow rate.

The functional metrics and the structural metrics obtained in either FIG. 3a or FIG. 3b are then fed into a comparator (306 or 356, respectively) which determines the level of similarity or lack thereof, or computes a combined third metric derived therefrom, and compares that third metric with similarly obtained metrics found in a reference database (307 or 357, respectively). This reference database could contain information of a normative nature. The comparison with the reference database is not required, and this step (307 or 357) could be skipped. The results of either approach may be displayed to a user (900) or stored for further analyses or comparison with future data similarly obtained and processed. An alternative to the comparator is to use a classifier or an expert system at this step, which is explained below.

While the preferred embodiments outlined below emphasize measurements of the FAZ, other retinal areas, aimed at particular pathologies, can also be targeted for this combined structural/functional approach. These include structural and functional observations of PED, AMD, exudates, and the optic nerve head, as outlined below.

FAZ structural metrics that are measurable include, but are not limited to, the area, or the diameter of the FAZ. Some methods for the determination of these structural observables or metrics are given in US Publication No. 2013/0301008 (hereby incorporated by reference). Other metrics that can be measured for the foveal pit include its size, area, diameter, slope, and depth (see for example, Chui et al. 2012; Dubis et al. 2009). The area would be preferably measured at a certain point within the foveal pit, and most preferably at the location where a specified retinal layer disappears at the boundary of the foveal pit. It has been shown that there is a strong relationship between foveal thickness, foveal shape, and neurovascular organization, and from the thinnest to the thickest fovea. Foveal structure varies from a shallow pit with the INL continuity through the center and a smallish FAZ to a deep pit overlaying only a thick ONL with a large FAZ. Models of the fovea demonstrate positive correlations between all of these metrics: FAZ size, axial length, degree of inner layer separation, and central foveal thickness (OS+ONL).

An alternative embodiment for step 303 in FIG. 3a (or for step 353 in FIG. 3b) would be to use a formula from a relationship created based on a reference or normative database to yield a metric that is correlated to the expected FAZ size with inputs that could include metrics of foveal pit morphology as outlined above.

A FAZ diameter or equivalent may be measured in several ways. One approach is to segment the various retinal layers, and choose those layers which disappear at the boundary of the foveal pit. These layers could be any one or all of: RNFL, GCL, IPL, and INL. A diameter could be defined as taking diagonally opposite points. While diameter here is generically defined as being determined at any azimuthal angle, a preferred definition is one that is measured from one or more horizontal B-scans at essentially the same lateral location. An alternative is to measure the area around the fovea over which the thicknesses of the GCL and the IPL (GCP+IPL) go to zero.

The OCT volumetric data set can be reduced to an enface image, by selectively integrating or otherwise generating a single representative value for the signal along the z-axis (based upon a selected range in z). Thus if there is a shallow pit, by selection or automatic determination of the appropriate z-range, the pit will be readily identifiable.

In another embodiment for step 303 of FIG. 3a, or step 353 of FIG. 3b, the FAZ diameter or similar metric can be identified by the increase in the ONL thickness which is below the maximum depth of the foveal pit.

In another embodiment, a plurality of OCT radial scans can be extracted from the OCT volumetric dataset obtained in step 303 of FIG. 3a or from step 353 of FIG. 3b. Each radial scan can then be analyzed by any of the aforementioned measurement methods. This will result in a plurality of points about the foveal pit boundary where the radial scan intersects that boundary. Adjacent points can then be joined by chords, and a multifaceted polygonal shape determined and the expected FAZ size determined. This expected size can then be superimposed upon the structural image or on the functional image.

Figure 4:
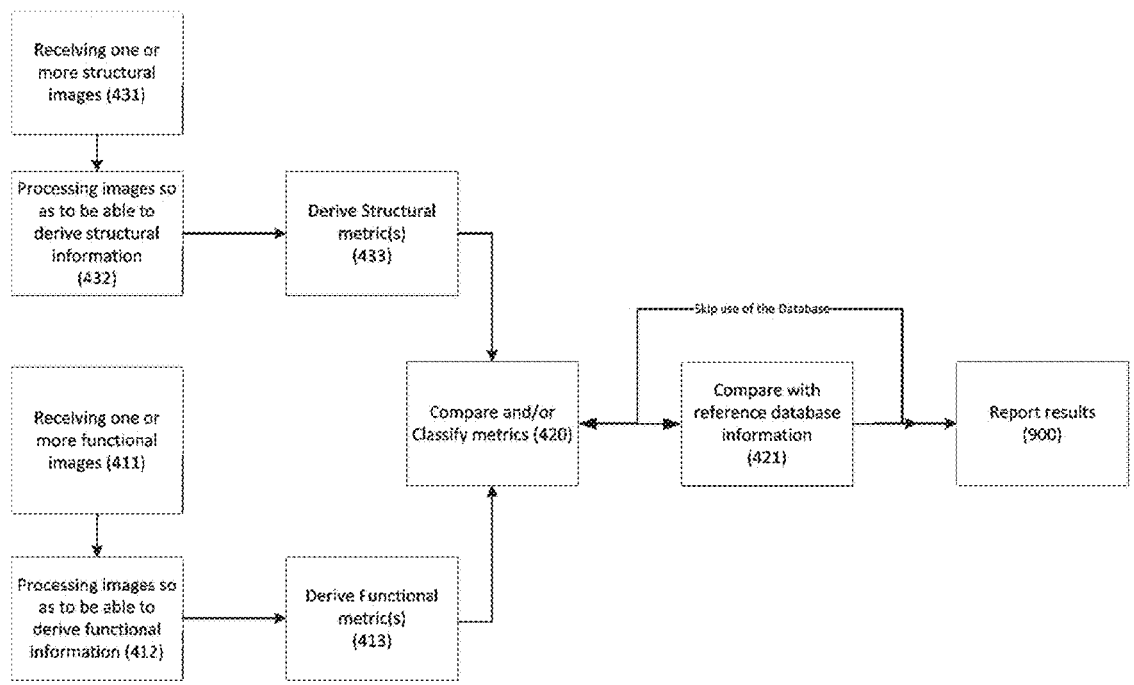
FIG. 4 is a flow chart of a basic embodiment in which a dataset from a structural imaging modality is processed to achieve structural measurements, and a dataset from a functional imaging modality is processed to achieve functional measurements.

In an alternative basic embodiment depicted in FIG. 4, a functional or angiographic imaging modality has produced images (411), either serially, concurrently, or at different times, of the same region of the eye as imaged using a structural imaging modality (431). The dataset from this functional/angiographic imaging modality is processed (412) to yield flow rates or flows or any metric that is detectably time dependent. These processed images yield functional metrics, e.g. such as the actual size of the FAZ (413), or any metric of any morphological or anatomical feature or features, preferably correlated, indicative of, or associated with pathologies.

The data from the structural imaging modality are analyzed or processed (432) to produce structural metrics (433), e.g., the expected size of the FAZ, or another anatomical feature. Similar to the embodiments of FIG. 3, both the structural and functional metrics obtained with the method of FIG. 4, are fed into a comparator and/or classifier (420) which discerns the level of discrepancy in the case of the comparator; and/or provides a classification from the classifier. A function of the comparator can be a comparison of the structural or functional metrics, or a combination thereof, with similar metrics contained within a reference or a normative database (421). This comparison with the database entries is optional.

The results of any of these computations or comparisons or results can then be reported or stored (900).

In any of the aforementioned embodiments, one or more structural metrics and one or more functional metrics are derived. These two different metrics (or sets of two different metrics or combinations of the metrics) are compared with each other, or to those similar metrics of a reference database, to establish the level of normalcy or the lack thereof. In the case of the diameters or areas of the FAZ derived from structural and functional imaging modalities, respectfully, a ratio of the structural to functional diameter, for example, for a normal eye would yield a unity value, or nearly thereto.

In eyes beset with DR or other pathologies, the ratio, or other mathematical combination of the metrics, could diverge from that metric associated with normalcy, depending upon the strength of the pathology. The earlier the images are obtained in the development of a disease, the closer to a normal value the structural or functional metrics, or a combination thereof, will be. Thus over time, as the pathology strengths or enlarges, the ratio, or other mathematical combination, will diverge from the reference or normal value to reveal disease progression.

While the ratio has been emphasized, other mathematical combinations (such as a normalized differential) of the structural and function metrics can be more sensitive to changes or disease prevalence. Such combined metrics could correlate better with disease presence, extent, or progression.

FAZ Measurements

Figure 5:
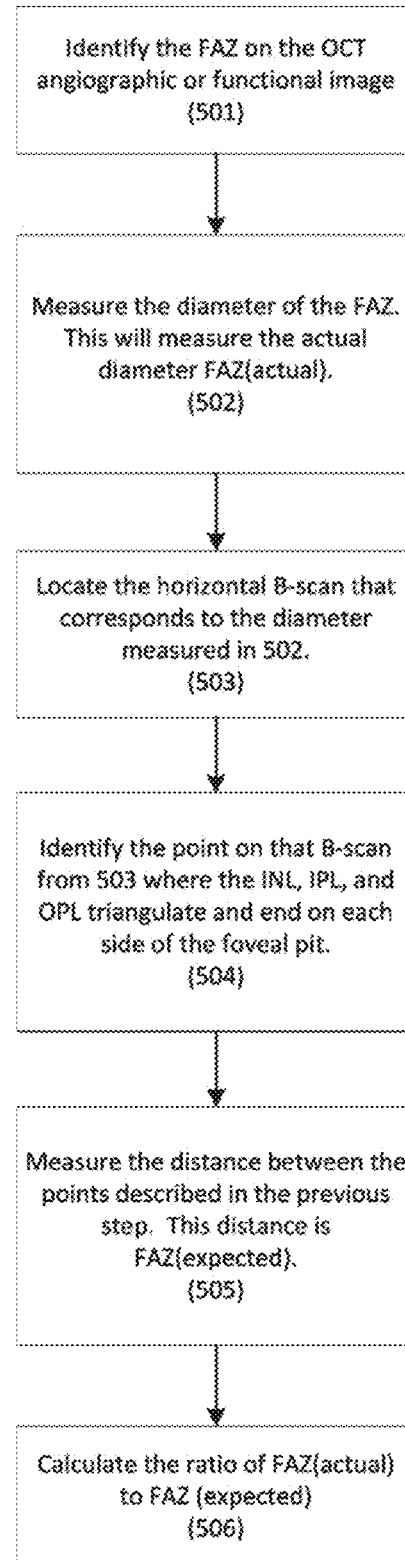
FIG. 5 is a flow chart of a preferred embodiment for the measurement of FAZ diameters (or similar metrics) from structural and functional OCT datasets and the comparison of the two values for a given eye.
Figure 6:
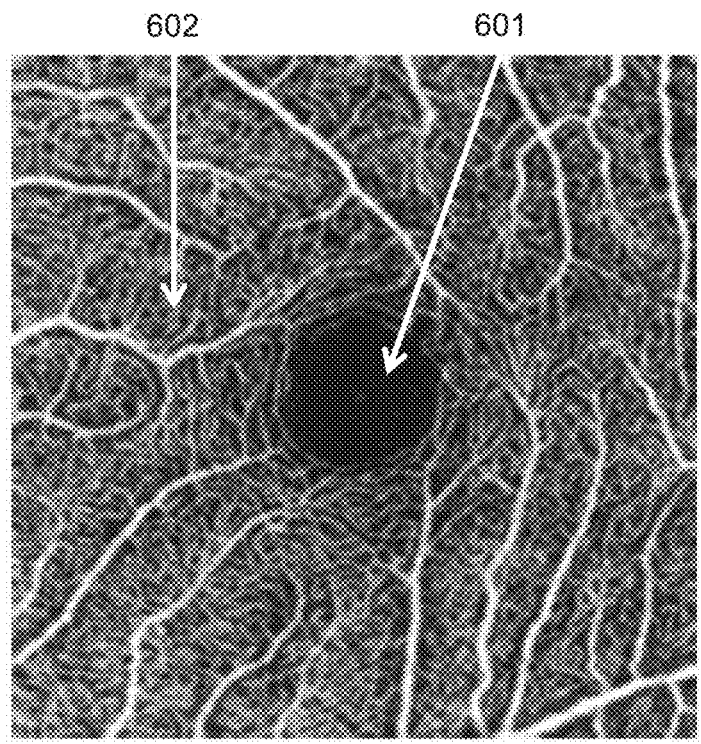
FIG. 6 is an image resultant from processing an OCT angiographic dataset taken of a normal macula. The FAZ (601) is indicated as is some of the retinal vasculature (602). The physical size of the image is 3×3 mm (255 pixels by 255 pixels). Lateral resolution is about 20 microns.
Figure 7:
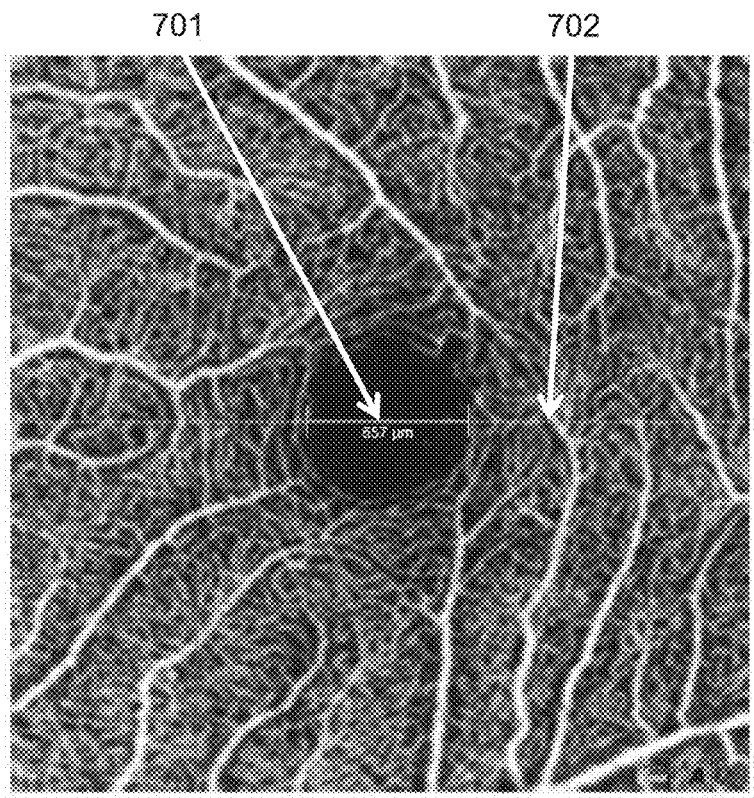
FIG. 7 is the same image as FIG. 6, but with the horizontal line (702) through the FAZ center indicated, and the resultant measurement of the FAZ diameter (701). The image is the same size as given in FIG. 6.
Figure 8:
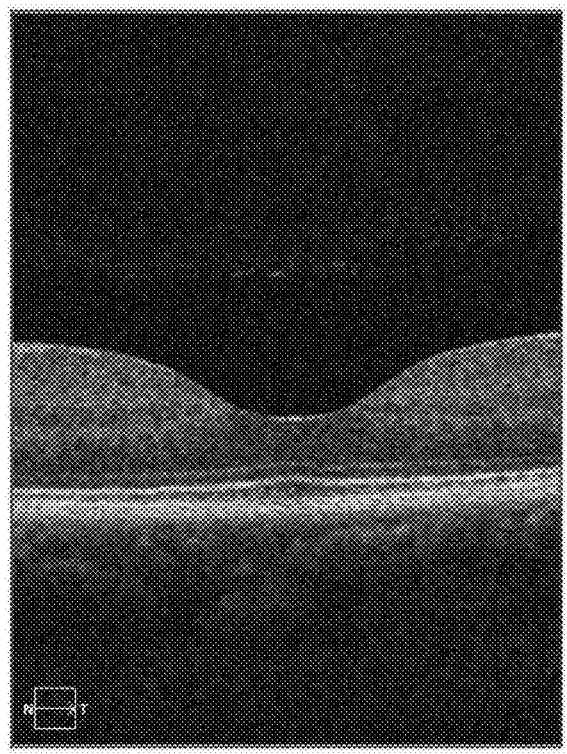
FIG. 8 is the B-scan associated with the horizontal line (702) in FIG. 7. From this B-scan, a structural diameter can be measured.
Figure 9:
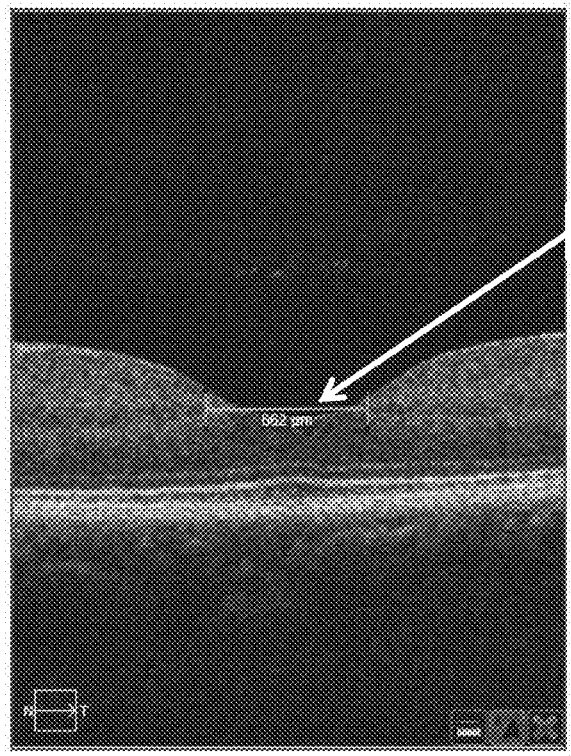
FIG. 9 is the same B-scan in FIG. 8, but with the measurement of the calipers so indicated.
Figure 10:
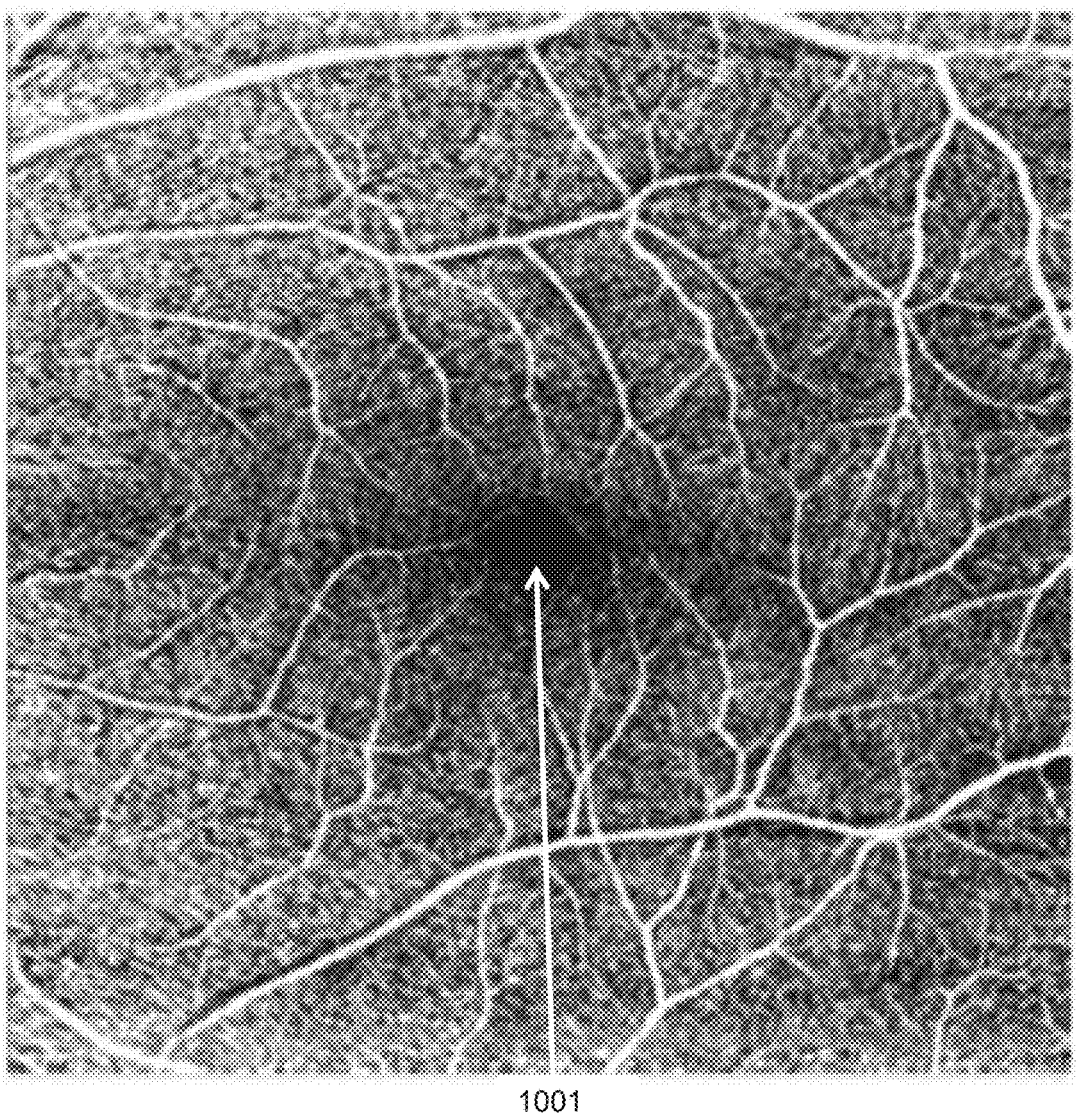
FIG. 10 is a functional image resultant from processing an OCT angiographic dataset taken of a diseased eye. The physical scan size is 6×6 mm (350 pixels by 350 pixels)
Figure 11:
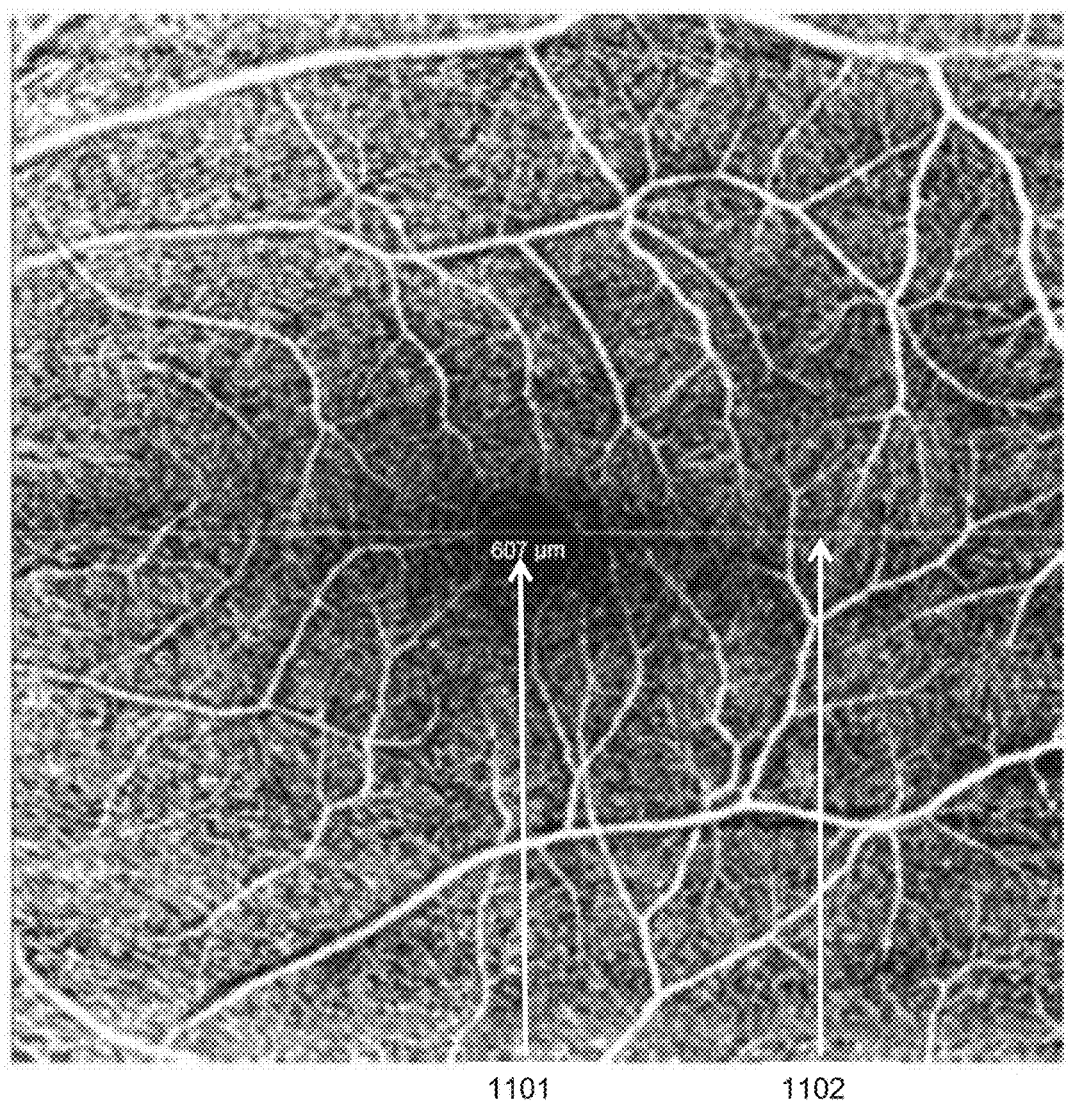
FIG. 11 is the same image as FIG. 10, but with the horizontal line (1102) through the FAZ center indicated, and the resultant measurement of the FAZ diameter (1101). This image has the same dimensions as that of FIG. 10.

A preferred embodiment to measure FAZ pathology is presented in FIG. 5 and presents the method of measuring specifically a diameter of the FAZ from both structural and functional data for both a normal eye (FIGS. 6-9), and for a diseased eye (FIGS. 10-13). The data of FIG. 6 are of a 3×3 mm field-of-view (FOV). The image is 255 pixels by 255 pixels. The data of FIG. 10 are of a 6×6 mm FOV and are 350 pixels by 350 pixels.

Figure 12:
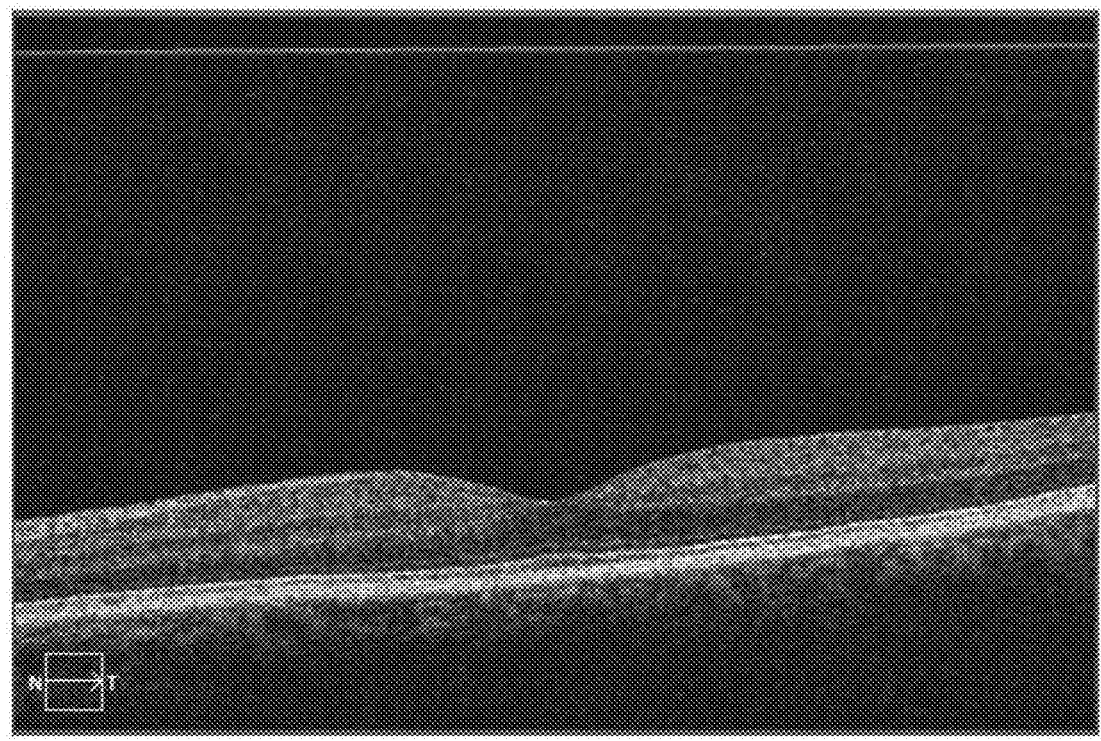
FIG. 12 is a structural B-scan associated with the horizontal line (1102) in FIG. 11. From this B-scan, a functional diameter can be measured.
Figure 13:
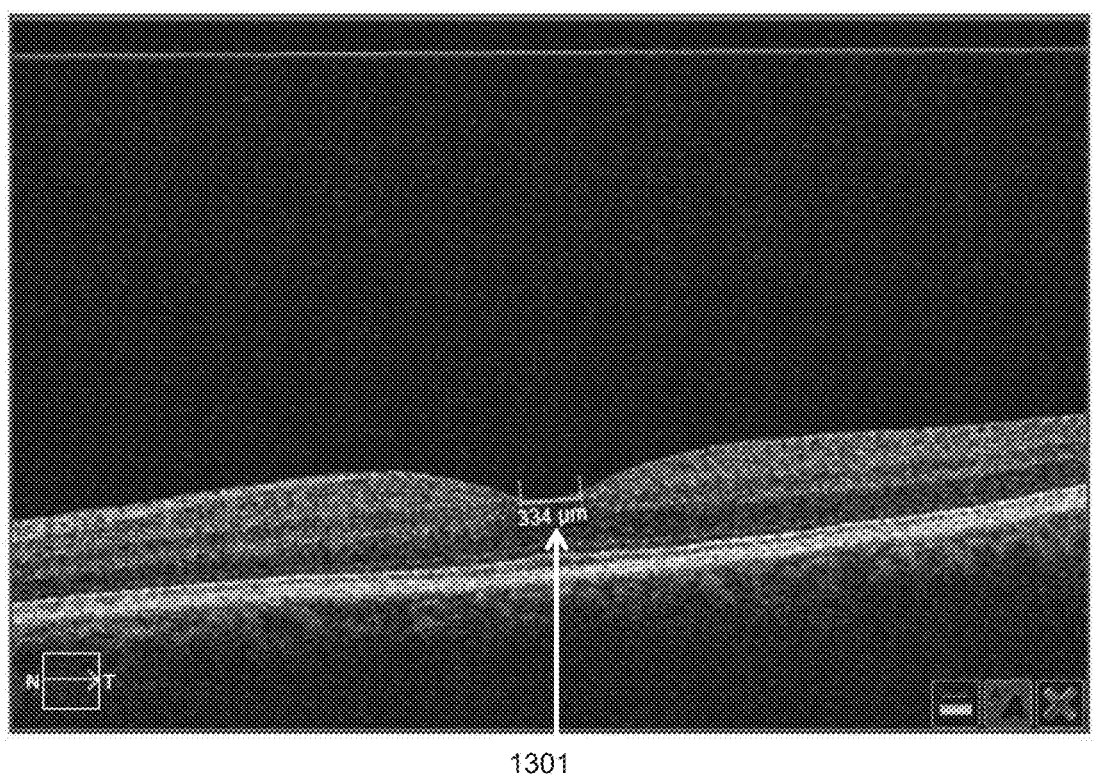
FIG. 13 is the same B-scan in FIG. 12, but with the measurement of the calipers so indicated.

In either case, normal or diseased, the method of FIG. 5 is applicable. The FAZ is identified (501) either automatically or manually on the functional image (601 on FIG. 6; 1001 on FIG. 10). (Item 602 in FIG. 6 is retinal vasculature, primarily consisting of capillaries.) A diameter is measured (502) along the horizontal line (702 in FIG. 7; 1102 in FIG. 11) through the center of the fovea (701 in FIG. 7; 1101 in FIG. 11). This measurement is the actual diameter of the FAZ=FAZ(act). The centroid of the FAZ usually aligns to the center of the fovea. In some instances, a difference in the centroid of the FAZ from the foveal center is indicative of asymmetry, which can be interpreted as loss of capillaries. A structural B-scan (see FIG. 8; FIG. 12) associated with the horizontal line (702 in FIG. 7; 1102 in FIG. 11) is also displayed (503) which allows the identification of the point on that B-scan where the INL, IPL, and OPL triangulate and end on each side of the foveal pit (504). The distance (505) between the points described in step 504 are measured along that horizontal (901 in FIG. 9; 1301 in FIG. 13). This is the expected FAZ size from structural data, or FAZ(exp).

These two measures, FAZ(act) and FAZ(exp), can be compared either directly or as a mathematical combination thereof (506), e.g., a ratio, to yield a disease metric. For example, the ratio (FAZ(act) to FAZ(exp)) for the normal eye (FIGS. 6-9) is 0.992. For the diseased eye (FIGS. 10-13), the ratio is 1.82, a distinct and decidedly measurable difference.

Given the large variation in FAZ morphologies and thus metrics even for people with normal eyes, either the structural or the functional information, each taken separately, may not have identified the pathological nature of the eye represented by the FIGS. 10-13.

Expert System

Given the number of scalar quantities, such as features (or metrics) that have been determined for one or more pathologies, an expert system can be developed to aid in diagnosis. These features or metrics would be both of a structural and functional nature. The approach is to define a feature vector, containing a plurality of these metrics (scalar quantities). The ensemble of feature vectors, a vector space, is an N-dimensional space. Usually at this point, there are one or more processes to reduce the dimensionality of the space— into a subspace. The dimensionality reduction techniques are well-known to the skilled person in the art of subspace generation. These feature vectors are then assembled into a matrix, and the eigenvectors/eigenvalues of this matrix are derived using canonical techniques well known to the ordinary skilled person. The eigenvectors and eigenvalues are the principal components of the hyperspace which identify those scalar properties that are most valuable in identifying properties of pathologies or any anatomical feature.

Utilizing a quantity of measurable features can only aid in achieving a more precise diagnosis, and preferably, an automated diagnosis. A more advanced approach, would be to produce a feature vector for each pixel, or an ensemble thereof.

The components of the feature vectors could include all of the aforementioned metrics, or a subset thereof: such as thicknesses, sizes, diameters, locations, reflectivities, intensity gradients, fluid flow gradients, direction or directions of fluid flows, rate of area or volume change over time, results from statistical analyses of features, and the locations and geometric properties of microaneurysms. In addition, patient information, such as age, can also be a component of the feature vector. Other features would be readily identifiable by the ordinary skilled person.

Upon assemblage of the feature vectors, an automatic classification by a machine learning algorithm can be performed. Optionally, exemplary regularization procedure can be used to produce smooth results. An exemplary classifier can produce a label for each input or feature vector. A specific type of the exemplary classifier can be a support vector machine (see, e.g., Cristianini and Shawe-Taylor 2000). Although, any supervised classifier would be appropriate in this case such as neural networks, naïve Bayesian, decision, trees, random forests, and k-nearest neighbor.

In machine learning, support vector machines (SVMs), also support vector networks) are supervised learning models with associated learning algorithms that analyze data and recognize patterns, used for classification and regression analysis. Given a set of training examples, each marked as belonging to one of two categories, an SVM training algorithm builds a model that assigns new examples into one category or the other, making it a non-probabilistic binary learning model. An SVM model is a representation of the examples as points in space, mapped so that the examples of the separate categories are divided by a clear gap that is as wide as possible. New examples are then mapped into that same space and predicted to belong to a category based on which side of the gap they fall on.

During training, this exemplary support vector machine can aim to generate a maximum margin between the classification boundary and the samples closest to this boundary. When given a new, unlabeled feature vector, the exemplary support vector machine can label that feature vector.

The classifier can be a linear classifier, given that its result is a linear combination of the inner product of the feature vector and the support vectors (eigenvectors mentioned above). However, by replacing the inner product by a kernel, a non-linear exemplary support vector machine can be constructed. Implicitly, the kernel can map the input features into a possibly very high dimensional space. In this feature space, a linear classification is performed. Various kernels can be used, such as, e.g., polynomial kernels, or radial basis functions.

In the methods of FIG. 3a, 3b, or 4, an option to the respective steps 307, 357, and 421 is a classifier, such as that described above. The reference databases of FIG. 3a, 3b, or 4 could represent the training data used to classify the feature vectors.

PED: Retinal Pigment Epithelium Detachment

PED structural information (or metrics) is derived from the segmentation of the RPE from that of the basement membrane to assess the level of detachment. Such information would be related to the location, volume, height, diameter, and area of the separation between the RPE and the basement membrane. With OCT systems, all of these observables are measurable.

Functional information obtainable is the flow rate of fluid creating the PED. Functional information would be any neovascular activity or any exudate activity, quantifiable by metrics, either manually or automatically determined. The level of these activities could be further clarified by repeat visits over time of the patient. This time progression is applicable to any pathology.

AMD: Age-related Macular Degeneration

Structural observables or metrics of AMD would initially be for the presence of drusen of any type, and could consist of location, area, diameter: their morphological characteristics. Functional observables of AMD include examining the drusen for any early signs of motion activity caused by the influx or movement of fluids. Wet AMD is a much more insidious form of AMD than dry. Drusen are spots scattered around the macula and are slight elevations between the RPE and the basement membrane. The contents are the residues of poorly phagocytized photoreceptors such as lipids and proteins.

Both structural and functional observations of the choriocapillaris or the RPE basement membrane will aid in identifying those areas of dry AMD that would be developing into wet AMD. The functional information would be able to differentiate between disciform scar tissue and neovascularized tissue. The use of structural and functional OCT in choroidal neovascularization is appropriate in either type (classic or occult).

Exudates

Structural observations would include locations and morphological characteristics. Functional observations would include the rate of change of the fluid leaking, thus providing a metric concerning the rate of progression of the disease or to gauge the level of activity.

Neovascularization Elsewhere (NVE)

NVE occurs at advanced stages of diabetic retinopathy. They are commonly observed using FA and color fundus photography, but currently there is no way to know which membranes are active and which are inactive. A combination of traditional fundus imaging with OCT angiography conveys key information about the location and activity of these membranes, which may aid in staging the disease as well as determining the treatment plan, which may include laser treatment of active membranes.

Optic Nerve Head Measurements

Quantification of microvasculature in the optic nerve head has been shown to correlate with the presence of glaucoma, and structural measurements of the optic nerve head are known to be one of the earliest signs of glaucomatous damage. Combining both types of information may allow improved diagnosis and monitoring of glaucoma. One specific example might be using the microvascular information to identify optic disc hemorrhages and doing detailed structural examinations over that part of the disc to look for sub-clinical thinning or rapid progression of RNFL thinning.

In the above description, for purposes of explanation, numerous specific details are set forth in order to provide a thorough understanding of the specification. It should be apparent, however, that the subject matter of the present application can be practiced without these specific details. It should be understood that the reference in the specification to "one embodiment", "some embodiments", or "an embodiment" means that a particular feature, structure, or characteristic described in connection with the embodiment is included in one or more embodiments of the description. The appearances of the phrase "in one embodiment" or "in some embodiments" in various places in the specification are not necessarily all referring to the same embodiment(s).

The foregoing description of the embodiments of the present subject matter has been presented for the purposes of illustration and description. It is not intended to be exhaustive or to limit the present embodiment of subject matter to the precise form disclosed. Many modifications and variations are possible in light of the above teaching. It is intended that the scope of the present embodiment of subject matter be limited not by this detailed description, but rather by the claims of this application. As will be understood by those familiar with the art, the present subject matter may be embodied in other specific forms without departing from the spirit or essential characteristics thereof.

The following references are hereby incorporated by reference:

NON-PATENT REFERENCES

Bresnick et al. 1984, Arch Opthal 202, 1286-1293.
Arend et al. 1995, Arch Opthal 113, 620-614.
Arend et al. 1997, IOVS 38, 1819-1824.
Sakata et al. 2006, Opthalmol 113, 1385-1391.
Sakata et al. 2007, Opthalmol 114, 2061-2069.
Tyrberg et al. 2008, Doc Ophthal 117, 185-189.
Otani et al. 2007, Opthalmol 114, 204-207.
Bolz et al. 2009, Opthalmol 116, 66-72.
Kim et al. 2012, IOVS 53, 85-92.
Springer & Hendrickson 2004a, Vis Neurosci 21, 53-62.
Springer & Hendrickson 2004b, Vis Neurosci 21, 775-790.
Springer & Hendrickson 2005, Vis Neurosci 22, 171-185.
Mariampillai et al. 2008, Opt Lett 33, 1530-1532.
Mariampillai et al. 2010, Opt Lett 35, 1257-1259.
Liu et al. 2013, J. Biomed Opt. 18, 060508.
Mahmud et al. 2013, J Biomed Opt 18, 050901.
Jia et al. 2011, Opt Exp 20, 4720-4725.
Zayit-Soudry et al. 2007, Surv Ophthalmol 52, 227-243.
Hartnett et al. 1992, Graefes Arch Clin Exp Ophthalmol. 230, 11-90.
Wang et al. 2007, Opt Exp 15, 4083-4097.
An & Wang 2008, Opt Exp 16, 11438-11452.
Fingler et al. 2007, Opt Exp 15, 12636-12653.
Fingler et al. 2009, Opt Exp 17, 22190-22200.
Abramoff et al. 2010, IEEE Trans Biomed Eng. 3, 169-208.
Sayegh et al. 2011, Ophthal 118, 1844-1851.
Gregori et al. 2011, Ophthalmology 118, 1373-1379.
Yehoshua et al. 2013, Ophth Surg Las Imag Ret 44, 127-32.
Stewart et al. 2003, IEEE Trans. Med. Imag. 22, 1379-1394.
Choi et al. 2013, PLoS One 8(12), e81499.
Fischer et al. 2012, PLoS One 7(4), e36155.
Dubis et al. 2009, Br J Opthalmol 93, 1223-1227.
Chiu et al. 2012, Optom Vis Sci 89, 602-620.
Gardiner et al. 2005, IOVS 46, 3712-3717.
Ferguson et al. 2004, Opt Exp 12, 5198-5208.
Vakoc et al. 2009, Nat. Med. 15, 1219-1223.
An et al. 2012, J Biomed Opt 17, 116018.
Zhao et al. 200; Opt Lett 25, 1358-1360 (2000).
Fingler et al. 2007, Opt Exp 15, 12637-12653.
Fingler et al. 2009, Opt Exp 17, 22190-22200.
Makita et al. 2006, Opt Exp 14, 7821-7840.
Wang et al. 2004, Opt Comm 242, 345-350.
Kim et al. 2011, Biomed Opt Exp 2, 1504-1513.
Lee 2012, IOVS 53, 164-70.
Stetson et al. 2013, IOVS 54, ARVO E-Abstract 6296.
Brar et al. 2009, Am J Ophthal 148, 439-444.
Huang et al. 1991, Sci 254, 1178.
Liu et al. 2011, Opt Exp 19, 3657-3666.
Lu & Chen 2010, J Biomed Exp 15, 016029.
Grulkowski et al. 2009, Opt Exp 17, 23726-23754.
Tao et al. 2009, Opt Exp 17, 4177-4188.
Wang et al. 2010, J Biomed Opt 15, 020502.
Wang et al. 2010, Opt Lett 35, 1467-1469.
Hong et al. 2007, Opt Exp 15, 7538-7550.
Huang et al. 1991, Science 254, 1178-1181.
Cristianini and Shawe-Taylor 2000, *An Introduction to Support Vector Machines and other kernel-based learning methods*, Cambridge, ISBN 0-521-78019-5.
Dubuis et al. 2009, Br J Opthal 93, 1223-1227.
Dmuchowska et al. 2012, Graefes Arch Clin Exp Opthal 252, 731-738.
Chui et al. 2014, 'Foveal Microvasculature and its Relationship to Retinal Thickness,' ARVO 2014, #5662.
Hageman, G. S. 2015, in 'Webvision: The Organization of the Retina and Visual System,' http://webvision.med.utah.edu/Patent

REFERENCES

US Publication No. 2005/0171438
US Publication No. 2012/0307014
US Publication No. 2012/0277579
U.S. Pat. No. 6,549,801
US Publication No. 2013/0176532
U.S. Pat. No. 8,857,988
US Publication No. 2012/0274898
US Publication No. 2012/0307014
US Publication No. 2008/0025570
U.S. Pat. No. 8,433,393
U.S. Pat. No. 7,301,644
US Publication No. 2014/0276025
US Publication No. 2013/0301008
US Publication No. 2010/0027857

What is claimed is:

1. A method to detect disease in the eye based on images obtained from the foveal avascular zone (FAZ) of the eye, said method comprising:
(a) collecting a plurality of images of the eye, including the FAZ of the eye, using an optical coherence tomography (OCT) system, said OCT system collecting both
(i) structural morphological or anatomical images and (ii) functional angiographic blood flow images, said functional images being obtained by collecting data at the same location in the eye at different times to permit analysis of motion;

(b) using an electronic processor, determining a size parameter of the FAZ based on an analysis of the structural images, said size parameter being either the diameter or the area of the FAZ;

(c) using an electronic processor, determining a size parameter of the FAZ based on an analysis of the functional images, said size parameter being the same as in step (b);

(d) using an electronic processor, comparing the size parameters determined in steps (b) and (c) to evaluate the state of disease in the eye; and (e) displaying the results of the comparison on a display or storing the results in an electronic processor for further analysis.

2. A method as recited in claim 1 wherein said comparison step (d) includes taking the ratio of the size parameters determined in steps (b) and (c).

3. A method as recited in claim 1 wherein the size parameter is a diameter of the FAZ, and wherein in step (c) the diameter is determined along a line though the center of the FAZ in the functional image and wherein in step (b) the line is used to define the location of a B-scan and wherein the B-scan is used to determine diameter of the FAZ in the structural analysis.

4. A method as recited in claim 3 wherein the diameter of the FAZ is determined in step (b) by identifying the points on the B-scan where the inner nuclear layer (INL), inner plexiform layer (IPL) and outer plexiform layer (OPL) end on each side of the foveal pit.

* * * * *

UNITED STATES PATENT AND TRADEMARK OFFICE
CERTIFICATE OF CORRECTION

PATENT NO. : 10,368,734 B2
APPLICATION NO. : 15/046878
DATED : August 6, 2019
INVENTOR(S) : Mary K. Durbin Page 1 of 1

It is certified that error appears in the above-identified patent and that said Letters Patent is hereby corrected as shown below:

In the Specification

Column 5, Line 24, delete "pixels)," and insert -- pixels). --, therefor.

Column 8, Lines 51-52, delete "indocyanian" and insert -- indocyanine --, therefor.

Signed and Sealed this
Eleventh Day of August, 2020

Andrei Iancu
*Director of the United States Patent and Trademark Office*